(12) United States Patent
Teran

(10) Patent No.: US 6,537,598 B1
(45) Date of Patent: Mar. 25, 2003

(54) METHOD FOR TENDERIZING RAW BEEF

(75) Inventor: James F. Teran, Highlands Ranch, CO (US)

(73) Assignee: Micro-Tender Industries, Inc., Denver, CO (US)

( * ) Notice: Subject to any disclaimer, the term of this patent is extended or adjusted under 35 U.S.C. 154(b) by 0 days.

(21) Appl. No.: 10/053,017

(22) Filed: Jan. 18, 2002

Related U.S. Application Data

(63) Continuation of application No. PCT/US01/30415, filed on Sep. 27, 2001.

(51) Int. Cl.$^7$ .............................. C12N 9/48; A23L 1/318
(52) U.S. Cl. .............................. 426/58; 426/56; 426/63; 426/574; 435/212
(58) Field of Search ........................... 426/56, 72, 241, 426/63, 58, 129, 302, 574, 641, 518, 519; 435/212

(56) References Cited

U.S. PATENT DOCUMENTS

| | | | |
|---|---|---|---|
| 2,140,781 A | 12/1938 | Allen | 99/107 |
| 2,321,623 A | 6/1943 | Ramsbottom et al. | 99/107 |
| 2,471,282 A | 5/1949 | Paddock | 99/107 |
| 2,999,020 A | 9/1961 | Williams | 99/107 |
| 3,147,123 A | 9/1964 | Komarik | 99/107 |
| 3,166,423 A | 1/1965 | Sleeth | 99/107 |
| 3,188,213 A | 6/1965 | Delaney | 99/107 |
| 3,533,803 A | 10/1970 | Schack et al. | 99/107 |
| 3,798,334 A | 3/1974 | Earl et al. | 426/58 |
| 4,066,790 A | 1/1978 | Connick et al. | 426/8 |
| 4,313,963 A | 2/1982 | Greenspan | 426/58 |
| 4,539,210 A | 9/1985 | O'Connell et al. | 426/56 |
| 5,512,015 A | 4/1996 | Teran | 452/141 |
| 6,015,580 A | 1/2000 | Mays | 426/281 |
| 6,040,013 A | 3/2000 | Karales | 427/281 |

*Primary Examiner*—Keith Hendricks
(74) *Attorney, Agent, or Firm*—David A. Farah; Sheridon & Mak PC

(57) ABSTRACT

An enzyme mixture for tenderizing raw beef comprising between about 98.7% and about 99.7% bromelin, between about 0.02% and about 0.08% ficin and between about 0.01% and about 0.05% papain. A method of tenderizing raw beef to produce a product that can be cooked by the consumer using the same methods as preparing naturally tender beef, and that results in a post-consumer preparation product that is consistently tender. The method comprises providing a suitable cut of raw beef and treating the raw beef with an enzyme mixture comprising between about 98.7% and about 99.7% bromelin, between about 0.02% and about 0.08% ficin and between about 0.01% and about 0.05% papain.

40 Claims, No Drawings

METHOD FOR TENDERIZING RAW BEEF

CROSS-REFERENCE TO RELATED APPLICATIONS

The present Application is a continuation of PCT Patent Application PCT/US01/30415 titled "Method for Tenderizing Raw Beef," filed Sep. 27, 2001, the contents of which are incorporated in this disclosure by reference in its entirety.

BACKGROUND

A large portion of commercially raised beef is limited in value because conventional preparation by the consumer generally results in meat that is unacceptably tough and dry. A variety of methods have been used to tenderize raw beef, such as mechanically interrupting the muscle fibers of the beef. However, none of these methods have produced a raw beef product that can be cooked by a human consumer using the same methods as preparing naturally tender beef, and that results in a post-consumer preparation product that is consistently tender and suitable for human consumption.

Therefore, it would be useful to have a method of tenderizing raw beef to produce a product that can be cooked by the consumer using the same methods as preparing naturally tender beef, and that results in a post-consumer preparation product that is consistently tender.

SUMMARY

According to one embodiment of the present invention, there is provided an enzyme mixture for tenderizing raw beef comprising bromelin, ficin and papain. In one embodiment, the enzyme mixture comprises between about 98.7% and about 99.7% bromelin, between about 0.02% and about 0.08% ficin and between about 0.01% and about 0.05% papain. In another embodiment, the enzyme mixture comprises between about 99% and about 99.4% bromelin, between about 0.04% and about 0.06% ficin and between about 0.02% and about 0.04% papain. In another embodiment, the enzyme mixture comprises 98.2% bromelin, 0.05% ficin and 0.03% papain.

According to another embodiment of the present invention, there is provided a composition for tenderizing raw beef. The composition comprises the enzyme mixture of the present invention. In one embodiment, the enzyme mixture is present in an amount of between about 0.5% and about 6% of the composition. In another embodiment, the enzyme mixture is present in an amount of between about 0.7% and about 2% of the composition. In another embodiment, the enzyme mixture is present in an amount of about 1% of the composition.

In a preferred embodiment, the carrier is NaCl. In one embodiment, the carrier is present in an amount of between about 25% and about 99%. In another embodiment, the carrier is present in an amount of between about 50% and about 99%. In another embodiment, the carrier is present in an amount of about 98.5%.

In another preferred embodiment, the composition further comprises a processing aid. In one embodiment, the processing aid is soybean oil. In a preferred embodiment, the processing aid is present in an amount of between about 0.1% and about 2%. In another preferred embodiment, the processing aid is present in an amount of between about 0.3% and about 1%. In another preferred embodiment, the processing aid is present in an amount of about 0.5%.

In a particularly preferred embodiment, the composition comprises about 98.4% carrier, about 1.1% enzyme mixture and about 0.5% processing aid.

According to one embodiment of the present invention, there is provided a method of tenderizing raw beef. The method comprises, first, providing a suitable cut of raw beef; and second treating the raw beef with an enzyme mixture according to the present invention.

In one embodiment, the raw beef provided is partially or completely skinned, boned or both. In another embodiment, the raw beef provided has waste products or excess fat removed.

In a preferred embodiment, the raw beef provided is an amount between about 0.1 kg to about 10,000 kg. In another preferred embodiment, the raw beef provided is an amount between about 100 kg and 6000 kg.

In one embodiment, treating the raw beef comprises injecting the raw beef with a solution containing the enzyme mixture. In another embodiment, treating the raw beef comprises injecting the raw beef with a solution comprising a composition that comprises the enzyme mixture. In a preferred embodiment, the composition additionally comprises a carrier. In another embodiment, the composition additionally comprises a processing aid.

In a preferred embodiment, the ratio of weight of the composition injected to the total weight of the beef being injected with the composition is between about 1:200 and about 1:1500. In a particularly preferred embodiment, the ratio of weight of the composition injected to the total weight of the beef being injected with the composition is between about 1:450 and about 1:650.

In one embodiment, the solution comprises the composition, ice, NaCl and potable water. In another embodiment, the solution injected is between about 6% and about 20% of the weight of the beef being injected. In a preferred embodiment, the solution injected is about 15% of the weight of the beef being injected.

In one embodiment, the method further comprises adding to the raw beef one or more than one substance selected from the group consisting of flavoring, NaCl, moisture enhancing agents, preservatives, and potable water. In another embodiment, the method further comprises tumbling the treated raw beef at a pressure and rotation speed selected to more evenly distribute the enzyme mixture or composition throughout the treated beef. In a preferred embodiment, the pressure is a near vacuum. In another preferred embodiment, the rotation speed is about between about 10 to about 15 revolutions per minute.

In one embodiment, the method further comprises exposing the treated raw beef to a relative vacuum in a closed container. In a preferred embodiment, the closed container is a polymer bag. In a particularly preferred embodiment, the relative vacuum is about −1.5 bar.

In one embodiment, the method further comprises packaging the treated raw beef in a commercial package. In another embodiment, the method further comprises distributing the treated raw beef to an intermediate wholesale or retail establishment.

DESCRIPTION

According to one embodiment of the present invention, there is provided an enzyme mixture that can be used to treat raw beef to produce a product that can be cooked by the consumer using the same methods as preparing naturally tender beef, and that results in a post-consumer preparation product that is consistently tender. The enzyme mixture comprises three enzymes: bromelin, ficin and papain. According to another embodiment of the present invention, there is provided a method of tenderizing raw beef to produce a product that can be cooked by the consumer using the same methods as cooking naturally tender beef, and that results in a post-consumer preparation product that is consistently tender. The method comprises treating the raw beef with an enzyme mixture according to the present invention. The enzyme mixtutre and method will now be disclosed in detail.

As used in this disclosure, "consumer" refers to the individual or enterprise that cooks the treated raw beef for eventual human consumption, and includes an individual at home, and a cook in a restaurant or a food service enterprise, among others as will be understood by those in the art with reference to this disclosure.

As used in this disclosure, percent amounts are given in percent by weight of total weight.

In one embodiment, the present invention is an enzyme mixture that can be used to treat raw beef according to the present invention. The enzyme mixture comprises three proteolytic enzymes, and can comprise one or more than one additional substance. Each enzyme in the enzyme mixture has a specific activation temperature and a deactivation temperature. When used to treat raw beef together and in the proper ratios, cooking the raw beef causes the enzymes to work synergistically to break down the substance of the raw beef and results in a post-consumer preparation product that is consistently tender and suitable for human consumption.

In a preferred embodiment, the enzyme mixture comprises three enzymes; bromelin, ficin and papain. In a particularly preferred embodiment, three enzymes are combined in specific ratios. Suitable enzymes can be obtained from All American Seasonings, Inc., Denver, Colo. US.

In a preferred embodiment, the enzyme mixture comprises between about 98.7% and about 99.7% bromelin, between about 0.02% and about 0.08% ficin and between about 0.01% and about 0.05% papain. In another preferred embodiment, the enzyme mixture comprises between about 99% and about 99.4% bromelin, between about 0.04% and about 0.06% ficin and between about 0.02% and about 0.04% papain. In a particularly preferred embodiment, the enzyme mixture comprises 98.2% bromelin, 0.05% ficin and 0.03% papain.

In one embodiment of the present invention, there is provided a composition for tenderizing raw beef. The composition comprises the enzyme mixture of the present invention and further comprises a carrier. The carrier assists in dispersing the enzyme mixture evenly in a solution and assists in preventing the enzyme mixture from clumping together and from hardening during storage. In a particularly preferred embodiment, the carrier is NaCl, available from All American Seasonings, Inc. though other salts, such as KCl or dextrose, or any other suitable carrier can be used, as will be understood by those with skill in the art with reference to this disclosure.

In another embodiment of the present invention, the composition further comprises a processing aid that assists in preventing the enzyme mixture from clumping together and from hardening during storage. In a particularly preferred embodiment, the processing aid is refined, bleached and odorless soybean oil (available from All American Seasonings, Inc.).

In a preferred embodiment, the enzyme mixture is present in an amount of between about 0.5% and about 6% of the composition. In another preferred embodiment, the enzyme mixture is present in an amount of between about 0.7% and about 2% of the composition. In a particularly preferred embodiment, the enzyme mixture is present in an amount of about 1% of the composition.

In a preferred embodiment, the carrier is present in an amount of between about 25% and about 99% of the composition. In another preferred embodiment, the carrier is present in an amount of between about 50% and about 99%. In a particularly preferred embodiment, the carrier is present in an amount of about 98.5%.

In a preferred embodiment, the processing aid is present in an amount of between about 0.1% and about 2%. In another preferred embodiment, the processing aid is present in an amount of between about 0.3% and about 1%. In a particularly preferred embodiment, the processing aid is present in an amount of about 0.5%.

According to a preferred embodiment of the present invention, the composition comprises 98.4% carrier, 1.1% enzyme mixture in the ratios given above, and 0.5% processing aid.

In another embodiment of the present invention, there is provided a method of tenderizing raw beef to produce a product that can be cooked by the consumer using the same methods as preparing naturally tender beef, and that results in a post-consumer preparation product that is consistently tender. In summary, the method comprises at least the following two steps. First, a suitable cut of raw beef is provided. Second, the raw beef is treated with an enzyme mixture according to the present invention.

The suitable cut of raw beef provided is preferably beef that is naturally tough rendering it unsuitable for human consumption after being cooked by conventional methods. In one embodiment, the raw beef is utility grade beef but other grades of beef that are naturally tough are also suitable. In a preferred embodiment, the raw beef selected is primarily of one cut. The raw beef can be partially or completely skinned, boned or both. Additionally, waste products, such as connective tissue, or excess fat can be removed. The amount of raw beef provided can be any amount that can be handled by equipment available to perform the method of the present invention. For example, the amount can be between about 0.1 kg to about 10,000 kg. In a preferred embodiment, the amount is between about 100 kg and about 6000 kg.

Treatment of the raw beef with an enzyme mixture according to the present invention can be accomplished using a variety of methods. In a preferred embodiment, the raw beef is injected with a solution containing the enzyme mixture using commercially available injection equipment, such as the Fomaco Injector, Robert Reiser Co., Canton, Mass. US, though any suitable injection equipmentcan be used as will be understood by those in the art with reference to this disclosure. Preferably, the sites of injection are less than about 7.5 cm apart. In a particularly preferred embodiment, the raw beef is injected with a solution containing the composition.

In one embodiment, the weight ratio of composition to raw beef is between about 1:200 and about 1:1500. In a preferred embodiment, the ratio of composition to raw beef is between about 1:450 and about 1:650.

For example, raw beef that is to be cooked by grilling or microwaving can be injected with a solution of the composition, ice, NaCl and potable water in a ratio of 1:13:1.7:55. Similarly, raw beef that is to be cooked by a convention gas or an electric oven can be injected with a mixture of the composition, ice, NaCl and potable water in a ratio of 1:20:2.5:80. The ice is used to cool the injection solution before injection to retard spoilage.

In one embodiment, the amount of the solution injected is between about 6% and about 20% of the weight of the beef being injected. In a preferred embodiment, the amount of the solution injected is about 15% of the weight of the beef being injected.

In a preferred embodiment, the method further comprises adding one or more than one substance selected from the group consisting of flavoring such as spices, NaCl, moisture enhancing agents such as sodium phosphate, preservatives such sodium lactate, and potable water to the raw beef to improve the taste, texture or other property of the finished product.

In another preferred embodiment, the method further comprises tumbling the treated raw beef at a pressure and rotation speed selected to more evenly distribute the enzyme mixture or composition throughout the treated beef. The pressure and rotation speed are chosen so as to separate the fibers of treated raw beef without shredding or tearing apart the fibers permanently, that is, while retaining the fibers' structural cohesiveness. In a preferred embodiment, the tumbling is performed in a near vacuum at between about 10 to about 15 revolutions per minute for between about 15 and about 30 minutes. The near vacuum combined with the rotation separates the muscle fibers of the treated raw beef allowing more rapid and uniform distribution of the enzymes. Preferably, the treated raw beef is tumbled in a finned vacuum tumbler with a central sealable chamber that can be operated at a specific pressure and rotation speed such as the Model LT30, available from Lance Industries, Allenton, Wis. US or a similar device, as will be understood by those with skill in the art with reference to this disclosure.

In another preferred embodiment, the method further comprises exposing the treated raw beef to a relative vacuum in a closed container. Containers are selected that can be sealed to maintain a vacuum for preserving the beef. In one embodiment, the container is a polymer bag, such as available from W. R. Grace & Co., Sioux City, Iowa. After selecting a suitable container, the treated raw beef is placed in the container and a vacuum is applied. In a preferred embodiment, the vacuum is a near vacuum of about −1.5 bar. The container tends to assume the shape of the beef upon application of the vacuum.

In another preferred embodiment, the method further comprises packaging the treated raw beef in a suitable commercial package for shipping and storage, or in a suitable commercial package for retail distribution to a consumer, or both. Packaging can include labeling as required by local laws and branding with a trademark or trade name and can include decorative wrapping for marketing purposes.

The treated raw beef can be distributed to an intermediate wholesale or retail establishment, and thereby to a consumer, or can be distributed directly to a consumer. After distribution, the consumer cooks the treated raw beef using the same methods as with naturally tender beef. For example, the treated raw beef can be removed from the packaging and container and can be barbecued, grilled, microwaved, prepared on a stove top or in an oven, or cooked using another which results in a post-consumer preparation product that is consistently tender and suitable for human consumption.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. An enzyme mixture for tenderizing raw beef, comprising between about 98.7% and about 99.7% bromelin, between about 0.02% and about 0.08% ficin, and between about 0.01% and about 0.05% papain.

2. The enzyme mixture of claim 1, comprising between about 99% and about 99.4% bromelin, between about 0.04% and about 0.06% ficin and between about 0.02% and about 0.04% papain.

3. The enzyme mixture of claim 1, comprising 98.2% bromelin, 0.05% ficin and 0.03% papain.

4. A composition for tenderizing raw beef, comprising the enzyme mixture of claim 1 and a carrier.

5. The composition of claim 4, where the enzyme mixture is present in an amount of between about 0.5% and about 6% of the composition.

6. The composition of claim 4, where the enzyme mixture is present in an amount of between about 0.7% and about 2% of the composition.

7. The composition of claim 4, where the enzyme mixture is present in an amount of about 1% of the composition.

8. The composition of claim 4, where the carrier is NaCl.

9. The composition of claim 4, where the carrier is present in an amount of between about 25% and about 99%.

10. The composition of claim 4, where the carrier is present in an amount of between about 50% and about 99%.

11. The composition of claim 4, where the carrier is present in an amount of about 98.5%.

12. The composition of claim 4, further comprising a processing aid.

13. The composition of claim 12, where the processing aid is soybean oil.

14. The composition of claim 4, where the processing aid is present in an amount of between about 0.1% and about 2%.

15. The composition of claim 12, where the processing aid is present in an amount of between about 0.3% and about 1%.

16. The composition of claim 12, where the processing aid is present in an amount of about 0.5%.

17. The composition of claim 12, comprising about 98.4% carrier, about 1.1% enzyme mixture and about 0.5% processing aid.

18. A method of tenderizing raw beef, the method comprising:
   a) providing a suitable cut of raw beef; and
   b) treating the raw beef with an enzyme mixture according to claim 1.

19. The method of claim 18, where the raw beef provided is partially or completely skinned, boned or both.

20. The method of claim 18, where the raw beef provided has waste products or excess fat removed.

21. The method of claim 18, where the raw beef provided is an amount between about 0.1 kg to about 10,000 kg.

22. The method of claim 18, where the raw beef provided is an amount between about 100 kg and 6000 kg.

23. The method of claim 18, where treating the raw beef comprises injecting the raw beef with a solution containing the enzyme mixture.

24. The method of claim 18, where treating the raw beef comprises injecting the raw beef with a solution comprising a composition that comprises the enzyme mixture.

25. The method of claim 24, where the composition additionally comprises a carrier.

26. The method of claim 24, where the composition additionally comprises a processing aid.

27. The method of claim 24, where the ratio of weight of the composition injected to the total weight of the beef being injected with the composition is between about 1:200 and about 1:1500.

28. The method of claim 24, where the ratio of weight of the composition injected to the total weight of the beef being injected with the composition is between about 1:450 and about 1:650.

29. The method of claim 24, where the solution comprises the composition, ice, NaCl and potable water.

30. The method of claim 24, where the solution injected is between about 6% and about 20% of the weight of the beef being injected.

31. The method of claim 24, where the solution injected is about 15% of the weight of the beef being injected.

32. The method of claim 18, further comprising adding to the raw beef one or more than one substance selected from the group consisting of flavoring, NaCl, moisture enhancing agents, preservatives, and potable water.

33. The method of claim 18, further comprising tumbling the treated raw beef at a pressure and rotation speed selected to more evenly distribute the enzyme mixture or composition throughout the treated beef.

34. The method of claim 33, where the pressure is a near vacuum.

35. The method of claim 33, where the rotation speed is about between about 10 to about 15 revolutions per minute.

36. The method of claim 18, further comprising exposing the treated raw beef to a relative vacuum a closed container.

37. The method of claim 36, where the closed container is a polymer bag.

38. The method of claim 36, where the relative vacuum is about −1.5 bar.

39. The method of claim 18, further comprising packaging the treated raw beef in a commercial package.

40. The method of claim 18, further comprising distributing the treated raw beef to an intermediate wholesale or retail establishment.

* * * * *